United States Patent [19]

Machida et al.

[11] Patent Number: 4,782,045

[45] Date of Patent: Nov. 1, 1988

[54] PROMOTING THE PROLIFERATION OF INTESTINAL BIFIDOBACTERIA

[75] Inventors: Yoshiaki Machida, Tokyo; Fumio Fukui, Naritashi; Takanobu Komoto, Funabashi, all of Japan

[73] Assignee: Showa Sangyo Co., Ltd., Tokyo, Japan

[21] Appl. No.: 853,976

[22] Filed: Apr. 21, 1986

[51] Int. Cl.$^4$ .............. A61K 35/74; A61K 31/70; A61K 31/715; A23C 9/152

[52] U.S. Cl. .............................. 514/23; 514/53; 514/61; 424/93; 536/4.1; 536/1.1; 435/244; 435/822

[58] Field of Search ............ 424/93; 435/244, 822; 514/53, 61, 23; 536/4.1, 1.1

[56] References Cited

U.S. PATENT DOCUMENTS

| | | |
|---|---|---|
| 4,021,544 | 5/1977 | Nair et al. ............... 536/4.1 |
| 4,201,772 | 5/1980 | Ingelman et al. ........... 514/54 |
| 4,435,389 | 3/1984 | Mutai et al. ............... 514/61 |
| 4,587,119 | 5/1986 | Bucke et al. .............. 514/53 |

FOREIGN PATENT DOCUMENTS

| | | | |
|---|---|---|---|
| 55-104885 | 8/1980 | Japan | 435/244 |
| 57-18982 | 1/1982 | Japan | 435/244 |
| 57-91193 | 6/1982 | Japan | 435/244 |
| 58-212780 | 12/1983 | Japan | 435/244 |
| 60-255731 | 12/1985 | Japan | 424/93 |

*Primary Examiner*—Ronald W. Griffin
*Assistant Examiner*—Nancy S. Carson
*Attorney, Agent, or Firm*—Oblon, Fisher, Spivak, McClelland & Maier

[57] ABSTRACT

The present invention provides a method for promoting the proliferation of microorganisms of the genus Bifidibacterium comprising contacting said microorganisms with a growth promoting effective amount of an isomalto-oligosaccharide.

16 Claims, No Drawings

PROMOTING THE PROLIFERATION OF INTESTINAL BIFIDOBACTERIA

BACKGROUND OF THE INVENTION

1. Field of the Invention

This invention relates to a method and an agent for promoting the proliferation of intestinal bifidobacteria using isomalto-oligosaccharides as an active substance.

2. Discussion of Background

Bifidobacteria, which belong to the genus Bifidobacterium, are known to be useful microorganisms inhabiting the human intestines. They have an important role in maintaining human health by preventing the increase of microorganisms which produce harmful substances, such as amines and ammonia, in the intestines.

In general, sugars are known nutrients for bifidobacteria as well as for noxious microorganisms, and sugars which are utilized only by bifidobacteria are little known. Additionally, it cannot be presumed from the properties of a sugar, such as molecular structure, whether the sugar will be utilized selectively by bifidobacteria or not.

The bifidobacteria proliferating action of sugars such as lactulose, raffinose, stachyose is well-known. Lactulose has found practical use in food. However, these sugars are consumed not only by bifidobacteria but also by the microorganisms which produce harmful substances in the intestines.

The bifidobacteria proliferating action of palatinose, an isomer of sucrose, and of fructo-oligosaccharides which consist of one sucrose unit and from one to four fructose units is also known. They are reported as useful bifidobacteria proliferating agents since they are utilized selectively by the bifidobacteria (Japan Kokai Nos. 91193/1982 and 53834/1984).

The inventors have made the surprising discovery that isomalto-oligosaccharides exhibit selective bifidobacteria proliferating action.

SUMMARY OF THE INVENTION

It is an object of this invention to provide a new bifidobacteria proliferation promoting substance which is selectively utilized by bifidobacteria and not by noxious microorganisms. The inventors have made the surprising discovery that isomalto-oligosaccharides are selectively utilized by bifidobacteria and not by noxious microorganisms.

DESCRIPTION OF THE PREFERRED EMBODIMENTS

The terms "isomalto-oligosaccharides" or "isomalto-sugars" are used herein as a general term for the oligosaccharides having branched structure and containing the $\alpha$-D-($1\rightarrow 6$) linkage of a glucose unit in the molecules. Isomaltose, isomaltotriose, panose, isomaltotetraose, and isomaltopentaose are typical sugars in this group, and are used alone or as mixtures in this invention.

They are prepared, for example, by reacting a sugar condensating enzyme such as glucoamylase with an aqueous solution of glucose with a concentration at least 50% by weight glucose (Japan patent application No. 245470/1984 and 61248/1985), or by reacting a sugar transfer enzyme such as $\alpha$-glucosidase with an aqueous solution of maltose, preferably with $\beta$-amylase and a starch debranching enzyme such as pullulanase (Japan patent application No. 58483/1985).

A syrup containing about 40% isomalto-sugar (to solid) can be obtained by the above methods. However it is possible to increase the content to over 60% by selecting the conditions appropriately. Sugars other than isomalto-sugars present in the syrup are mainly glucose and maltose.

A typical composition of isomalto-oligosaccharide in the syrup thus obtained is 20 to 30% isomaltose, 10 to 15% panose, isomaltotriose and other trioses, and 5 to 10% isomaltotetrasose and saccharides which consist of four or more glucose units.

A syrup containing mainly saccharides consisting of three or more glucose units can also be produced by reacting a sugar transfer enzyme with the starch which has been hydrolyzed by a starch debranching enzyme and $\alpha$-amylase (Japan Patent application No. 53017/1985). The isomalto-sugar composition of the product is from 10 to 25% isomaltose, 20 to 35% panose, isomaltotriose and other trioses, and from 5 to 15% isomaltotetrasose and saccharides consisting of four or more glucose units.

The isomalto-oligosaccharide syrup thus obtained can be further subjected to the following treatments in order to increase the concentration of isomalto-sugars to about 90% or more relative to the solid.

(1) Concentrating and cooling the syrup slowly to crystallize out glucose, etc., and thereby remove them from the syrup.

(2) Adding sodium chloride into the syrup to crystallize out a glucose-sodium chloride complex and thereby remove them from the syrup.

(3) Adding an organic solvent such as alcohols, acetone, etc., into the syrup to precipitate sugars othe than isomalto-oligosaccharides and thereby remove them.

(4) Removing sugars other than isomalto-oligosaccharides from the syrup by chromatographic separation techniques.

(5) Removing sugars other than isomalto-oligosaccharides from the syrup by yeast fermentation.

The sugar composition of concentrated isomalto-oligosaccharides thus obtained are as follows:

TABLE 1

| Principal component | Isomaltose (%) | Isomalto-sugar comprising three or more glucose units (%) |
|---|---|---|
| Isomaltose | 40~70 | 25~35 |
| Panose, isomaltotriose and other trioses | 15~30 | 40~50 |
| Isomaltotetraose and saccharides consisting of four or more glucose units | 10~20 | 15~20 |

These isomalto-sugar syrups are further treated, if necessary, by gelfiltration or an ion exchange resin column to fractionate the sugars by the number of glucose units. Fractions consisting of isomalto-disaccharides, mainly isomaltose; isomalto-trisaccharides, mainly panose and isomaltotriose; and isomalto-tetrasaccharides, mainly isomaltotetraose, can be obtained separately, and they are also active as bifidobacteria proliferating agents.

The isomalto-sugar syrup or the separated fractions may further be powdered by well-known methods such as, for example, spray drying and adsorbing on a carrier.

The bifidobacteria proliferation promoting action of the isomalto-oligosaccharides was examined as follows.

Several kinds of microorganisms including those in the genus Bifidobacterium were incubated in sterilized culture media consisting of peptone yeast-Fildes solution (hereinafter referred to as "PYF medium") into which were added 0.5 weight % of the sugars tested.

1. Culture Medium

The composition of PYF medium (pH 7.2) is as follows:

| | |
|---|---|
| Pancreatic digest of casein (BBL Trypticase peptone made by Becton Dickinson and Company) | 10 grams |
| Yeast extract (made by Difco company) | 5 grams |
| Fildes solution | 40 milliliters |
| Salts solution | 40 milliliters |
| $CaCl_2$ (anhydrous) | 0.2 grams |
| $MgSO_4$ | 0.2 |
| $K_2HPO_4$ | 1.0 |
| $KH_2PO_4$ | 1.0 |
| $NaHCO_3$ | 10.0 |
| NaCl | 2.0 |
| Pure water | 1,000 milliliters |
| L-Cysteine.HCl.$H_2O$ | 0.5 grams |
| Pure water | 920 milliliters |

Fildes solution is prepared by mixing the following components, digesting the mixture for one night in a bath maintained at 55° C., adding 12 milliliters of 20% aqueous solution of NaOH, and adjusting the pH at 7.6 by NaOH.

| | |
|---|---|
| Physiological saline (0.85% aqueous solution of NaCl) | 150 milliliters |
| Concentrated hydrochloric acid | 6 milliliters |
| Horse blood | 50 milliliters |
| Pepsine, 1/10,000 aqueous solution (Difco Co.) | 1 gram |

2. Method and Result

Fresh microorganisms incubated on agar plate culture media were innoculated at $10^8$ cfu (colony formation unit) per each test tube of PYF medium, in which the sugars examined were added at a concentration of 0.5 weight %. The test tubes were incubated at 37° C. for 48 hours under anaerobic conditions by the steel-wool method. The absorbance of the resultant liquid at 650 nanometers was determined and the consumability of the tested sugars by the microorganisms was calculated by the following equation:

$$RG = \frac{OD \text{ for tested sugar} - OD \text{ for } PYF \text{ medium}}{OD \text{ for glucose} - OD \text{ for } PYF \text{ medium}} \times 100$$

RG: rate of growth
OD: optical density

The results are shown in Table 2, in which the signs represent the following RG values.
++ = RG ≧ 75
+ = 50 ≦ RG < 75
± = 25 ≦ RG < 50
− RG < 25

TABLE 2

| Microorganisms | Glucose | Maltose | Lactose | Raffinose | 90% mixt.* | Isomaltose | Triose** | Tetraose*** |
|---|---|---|---|---|---|---|---|---|
| Bifidobacterium adolescentis E298 | ++ | ++ | ++ | ++ | ++ | ++ | ++ | ++ |
| Bifidobacterium infantis I-10-5 | ++ | ++ | ++ | ++ | ++ | ++ | ++ | ++ |
| Bifidobacterium breve SI | ++ | ++ | ++ | ++ | ++ | ++ | ++ | ++ |
| Bifidobacterium longum E194 | ++ | ++ | ++ | ++ | ++ | ++ | ++ | ++ |
| Lactobacillus acidophilus ATCC4356 | ++ | + | ++ | − | − | − | − | − |
| Clostridium paraputrificum | ++ | ++ | ++ | − | − | − | − | − |
| Clostridium SP2 | ++ | + | ± | − | − | − | − | − |
| Bacteroides vulgatus | ++ | ++ | ++ | + | − | ± | − | − |
| Bacteroides ovatus | ++ | ++ | ++ | + | − | − | − | − |
| Escherichia coli | ++ | ++ | ± | ++ | − | − | − | − |
| Peptostreptococcus anaerobius X-36 | + | − | − | ++ | − | − | − | − |
| Fusobacterium varium VI-43 | ++ | − | − | − | − | − | − | − |

*The 90% mixture contains 90% of isomalto-oligosaccharides to the solid and the composition is as follows:
Isomaltose 50%
Isomalto-trisaccharides (isomaltotriose, panose, etc.) 25%
Other isomalto-sugars 15%
Sugars other than isomalto-sugars (mainly glucose and maltose) 10%
**Over 85% (to the solid) of triose mainly panose and isomaltotriose.
***Over 85% (to the solid) of tetraose mainly isomaltotetraose.

The isomalto-sugars as well as the other sugars are consumed by the microorganisms of the genus bifidobacteria. However, most microorganisms other than bifidobacteria do not consume the isomalto-sugars, as is seen in Table 2. Thus, it is apparent that the isomalto-sugars are consumed selectively by the bifidobacteria.

Raffinose is not consumed by some of the microorganisms, such as the genus Clostridium or the genus Fusobacterium, while other sugars such as glucose and lactose are consumed by all microorganisms. However, Raffinose is consumed by Escherichia coli and the genus Bacteroides which are the microorganisms which produce harmful substances in the intestine. The selectivity of Raffinose is apparently lower than the selectivity of isomalto-sugar for bifidobacteria.

The isomalto-sugars are selective and efficient bifidobacteria proliferating agents. The isomalto-sugars may be used singly, as a mixture with foodstuffs, as a raw material or with a pharmaceutically acceptable diluent in the forms such as, for example, a powder, granule, tablet, sugar-coated tablet, capsule, suspension, solution, emulsion or ampoule. As an active ingredient, the isomalto-sugars are present from about 0.1 to 100% by weight in the proliferating agent which is taken orally or parenterally according to this invention.

The amount suitable for oral intake of the proliferating agent is in the range from about 0.01 to about 2.0 grams/kg of body weight per day, preferably 0.1 to 1.5 g/kg/day, although it varies depending on individual differences.

Bifidobacteria may be admixed with the proliferating agent in order to increase the proliferation promoting action. For this purpose, dried cells of the microorganisms belonging to the genus Bifidobacterium are used at about 30 to 70 parts by weight to about 70 to 30 parts by weight of the isomalto-oligosaccharides solid.

Vitamins, i.e. pantetheine, pantothenic acid, and riboflavin are also known as essential substances for the growth of Bifidobacterium, and therefore, their use together with the isomalto-oligosaccharides is effective to increase the growth of Bifidobacterium in the intestines. Suitable amounts of these vitamins are from about 1/100 to 1/300 to the weight of the isomalto-oligosaccharides.

Other features of the invention will become apparent in the course of the following descriptions of exemplary embodiments which are given for illustration of the invention and are not intended to be limitlng thereof.

EXAMPLE 1

Bread was made by straight process with the following composition:

| Composition | Control | Test |
| --- | --- | --- |
| Wheat flour | 500 gr | 500 gr |
| Sucrose | 100 | 50 |
| 55% fructose syrup | 33 | 33 |
| Isomalto-sugar** | 0 | 66 |
| Whole egg | 50 | 50 |
| Shortening | 30 | 30 |
| Dried yeast | 10 | 10 |
| Yeast food | 0.5 | 0.5 |
| Salt | 3 | 3 |
| Water | 217 | 201 |

*Moisture 25%. "Sunfruct" made by Sanmatsu Kogyo Co.
**Moisture 24.2% and about 50% of isomaltooligosaccharides to the solid.

Dough was prepared by the following steps:

(1) Activate yeast prior to use by mixing warm water with the mixture of dried yeast and a small amount of sucrose.

(2) Mix sugar including isomalto-sugar syrup, egg, yeast food, salt and half of the required flour in a mixing bowl, and knead the mixture at 160 rpm for 1 minute.

(3) Add yeast and knead at 160 rpm for 3 minutes.

(4) Add the rest of the flour and knead at 160 rpm for 1 minute and then at 230 rpm for 3 minutes.

(5) Add shortening and knead at 230 rpm for 4 minutes to obtain the dough.

Fermentation and baking were carried out as follows:

(1) Place the dough in a thermo-hygrostst at 29° C. temperature and 90 to 100% relative humidity for 2 hours.

(2) Punch (degas) the dough and place it in the same conditions for 1 hour.

(3) Punch ag in and further ferment it in the same conditions for 20 minutes.

(4) Cut the dough into 50 gram pieces.

(5) Bench at 30 to 31° C. for 20 minutes.

(6) Proof at 36 to 37° C. for 60 minutes.

(7) Bake at 180° C. for 10 minutes.

The moisture content of the bread using the isomalto-oligosaccharides ("test") was stable during the preservation and staling was considerably retarded. Taste, texture of the crumbs, etc. were also excellent as compared to the bread of the "control".

EXAMPLE 2

Fifty parts of spray dried isomalto-oligosaccharides containing about 90% isomalto-sugar were admixed with 5 parts of magnesium stearate, 25 parts of corn starch and 20 parts of lactose and made into a tablet. The composition of isomalto-oligosaccharides was as follows:

| Isomaltose | 28% |
| --- | --- |
| Panose and Isomaltotriose | 45 |
| Isomaltotetraose and others | 17 |

EXAMPLE 3

(1) The bread prepared in Example 1 was fed to 20 male and female volunteers ages between 25 and 35 years old. The volunteers were divided into two groups, and the bread "control" was fed to the first group and the bread "test" to the other. The daily intake of isomalto-oligosaccharides was about 6 grams for the "test" group. The feeding continued for 4 weeks. Feces samples were collected from the 20 persons at the beginning and the final days of the period, and the numbers of microorganisms in the samples were determined.

It was observed that the number of microorganisms belonging to the genus Bifidobacterium increased about 100 times by comparing the samples from the beginning and the final days of the "test" group, while the number was unchanged in the "control" group. The numbers of the microorganisms other than bifidobacteria such as the genus Clostridium, *Escherichia coli*, etc. on the final day were relatively lower than the beginning in the "test" group.

(2) The tablet prepared in Example 2 was fed to 10 male vounteers ages between 65 and 80 years old, with a daily intake of 20 grams of isomalto-sugar, for 60 days. The numbers of microorganisms in the feces collected from all the members were determined every 5 days from the beginning of the feeding. An increase in the number of bifidobacteria during the whole period was observed for 7 persons, and for three members of this group the number of bifidobacteria was very high. No increase was observed for one person, while a very slight increase was observed for two of the remaining three persons.

Obviously, numerous modifications and variations of the present invention are possible in light of the above teachings. It is therefore to be understood that within the scope of the intended claims, the invention may be practiced otherwise than as specifically described herein.

What is claimed as new and desired to be secured by Letters Patent of the United States is:

1. A method for promoting the proliferation of microorganisms of the genus Bifidobacterium, comprising contacting said microorganisms with a growth promoting effective amount of an isomalto-oligosaccharide.

2. The method of claim 1, wherein said isomalto-oligosaccharide is isomaltose.

3. The method of claim 1, wherein said isomalto-oligosaccharide is panose.

4. The method of claim 1, wherein said isomalto-oligosaccharide is isomaltotriose.

5. The method of claim 1, wherein said isomalto-oligosaccharide is isomaltotetraose.

6. The method of claim 1, wherein said isomalto-oligosaccharide is a mixture of at least two sugars selected from the group consisting of isomaltose, panose, isomaltotriose, and isomaltotetraose.

7. The method of claim 1, wherein said contacting occurs in a human by ingesting about 0.01 to about 2.0 grams per kg of body weight per day of said isomalto-oligosaccharide.

8. The method of claim 7, wherein said isomalto-oligosaccharide is isomaltose.

9. The method of claim 7, wherein said isomalto-oligosaccharide is panose.

10. The method of claim 7, wherein said isomalto-oligosaccharide is isomaltotriose.

11. The method of claim 7, wherein said isomalto-oligosaccharide is isomaltotetraose.

12. The method of claim 7, wherein said isomalto-oligosaccharide is a mixture of at least two sugars selected from the group consisting of isomaltose, panose, isomaltotriose, and isomaltotetraose.

13. The method of claim 7, further comprising premixing 30–70 parts by weight of cells of microorganisms of the genus Bifidobacterium to 70–30 parts by weight of said isomalto-oligosaccharide before said feeding step.

14. An agent for promoting the proliferation of microorganisms of the genus Bifidobacterium, comprising an isomalto-oligosaccharide, and further comprising 30–70 parts by weight of cells of microorganisms of the genus Bifidobacterium to 70–30 parts by weight of said isomalto-oligosaccharide.

15. The agent of claim 14, further comprising 1 part by weight of a vitamin to 100–300 parts by weight of said isomalto-oligosaccharide.

16. The agent of claim 15, wherein said vitamin is at least one member selected from the group consisting of pantheteine, pantothenic acid, and riboflavin.

* * * * *